United States Patent [19]

Froehler

[11] Patent Number: 5,399,676
[45] Date of Patent: Mar. 21, 1995

[54] OLIGONUCLEOTIDES WITH INVERTED POLARITY

[75] Inventor: Brian Froehler, Belmont, Calif.

[73] Assignee: Gilead Sciences, Foster City, Calif.

[21] Appl. No.: 559,958

[22] Filed: Jul. 30, 1990

Related U.S. Application Data

[63] Continuation-in-part of Ser. No. 502,272, Mar. 29, 1990, abandoned, which is a continuation-in-part of Ser. No. 425,803, Oct. 23, 1989, abandoned.

[51] Int. Cl.$^6$ .................. C07H 21/02; C07H 21/04; C12Q 1/68
[52] U.S. Cl. ........................... 536/23.1; 435/6; 536/24.5; 536/28.4; 536/26.7; 536/24.3
[58] Field of Search ........... 536/27, 28, 24.5, 28.4, 536/26.7, 23.1, 24.3; 435/6; 514/44

[56] References Cited

U.S. PATENT DOCUMENTS

| | | | |
|---|---|---|---|
| 4,894,325 | 1/1990 | Englehardt et al. | 435/6 |
| 4,957,858 | 4/1988 | Chu et al. | 435/6 |

FOREIGN PATENT DOCUMENTS

| | | |
|---|---|---|
| 0227976 | 7/1987 | European Pat. Off. . |
| 0375408 | 6/1990 | European Pat. Off. . |

OTHER PUBLICATIONS

Gilman, Bichemistry (1968) 7(8):28–09–2813.
Moser et al., *Science* (1987) 238:645–650.
Cooney et al., *Science* (1988) 241:456–459.
Capobianco et al., *Nucleic Acids Res.* (1990) 18(9):2661–2669.
Horne et al., *J. Amer. Chem. Soc.* (1990) 112:2435–2437.
Van De Sande et al., *Science* (1988) 241:551–557.
Praseuth, D., et al., *Proc. Natl. Acad. Sci. USA* (1988) 85:1349–1353.
Gilham Adv. Exp. Med. Biol. 42:173–185 (1974).
Chu et al *Nucleic Acids Res* 11(18):6513–29 (1983).
Chu et al *Nucl Acids Res* 14(14):5591–03 (1986).

*Primary Examiner*—Mindy B. Fleisher
*Attorney, Agent, or Firm*—Morrison & Foerster

[57] ABSTRACT

Oligonucleotides having tandem sequences of inverted polarity, i.e., oligonucleotides comprising regions of the formula:

$$3' \text{-----} 5' \text{--} C \text{--} 5' \text{-----} 3' \quad (1)$$

or $$5' \text{-----} 3' \text{--} C \text{--} 3' \text{-----} 5' \quad (2)$$

wherein —C— symbolizes any method of coupling the nucleotide sequence of opposite polarity, are useful for forming an extended triple helix with a double-helical nucleotide duplex. The inverted polarity also stabilizes the single-strand oligonucleotides to exonuclease degradation.

32 Claims, 2 Drawing Sheets

OLIGONUCLEOTIDES WITH INVERTED POLARITY

This is a continuation-in-part of U.S. patent application Ser. No. 502,272, filed 29 Mar. 1990, abandoned, which is a continuation-in-part of U.S. patent application Ser. No. 425,803, filed 23 Oct. 1989, abandoned.

TECHNICAL FIELD

The invention is directed to oligonucleotides having tandem sequences of inverted polarity. These oligonucleotides are useful for forming triple helices with double-stranded duplex DNA. The oligomers with inverted polarities allow a first sequence of the oligonucleotide to bind to a segment on one strand of a target duplex, and a second sequence with inverted polarity sequence to bind to a segment on the other strand of the duplex. Also, the invention oligonucleotides may be stabilized by this inversion of the polarity which presents an unnatural terminus or internal linkage, thereby avoiding potential damage by nucleases.

BACKGROUND ART

Oligonucleotides are known to be able to bind to double-helical DNA in the major groove of the helix, thereby forming a triple helix structure. The code for binding to form a triple helix (hereinafter referred to as the triple helix code) does not follow the same code as that for the binding of two single-stranded polynucleotides to form a double helix. The code for triple helix formation is set forth, for example, in Moser, H. E. and Dervan, P. B., *Science* (1987) 238: 645–650, and in Coohey, M., et al., *Science* (1988) 241:456–459. According to this code, isomorphous base triplets (T-A-T and C-G-C+) can be formed between any homopurine-homopyrimidine duplex and a corresponding, third, homopyrimidine strand. Since the rules limit the sequences which can form a triple helix it would be desirable to obtain oligonucleotides which can bind to form a triple helix in one portion of a duplex and cross over the groove in the double helix to bind to another portion of the duplex, thereby extending the portion of the duplex which can be "read." Such oligonucleotides would allow for identification and location of unique portions of double-helical DNA similar to the manner in which unique portions of single-stranded DNA are identified and located by single-stranded oligonucleotides.

The invention provides oligonucleotides which have inverted polarities for at least two regions of the oligonucleotide, thereby allowing the respective inverted polarity segments to read complementary strands of a double-helical duplex. By "inverted polarity" is meant that the oligonucleotide contains tandem sequences which have opposite polarity, i.e., one having polarity 5'→3' followed by another with polarity 3'→5', or vice versa. This implies that these sequences are joined by linkages which can be thought of as effectively a 3'—3' internucleotide junction, (however the linkage is accomplished), or effectively a 5'—5' internucleotide junction. Such oligomers have been suggested as by-products of reactions to obtain cyclic oligonucleotides by Capobianco, M. L. et al., *Nucleic Acids Res* (1990) 18: 2661–2669.

DISCLOSURE OF THE INVENTION

The ability of oligonucleotide sequences to hybridize to double-stranded duplex DNA is enhanced by providing oligonucleotides with inverted polarity so that the binding oligonucleotide can skip from one complementary strand in the duplex to the other as its polarity shifts. In its simplest embodiment, there is a single inversion of polarity in the binding oligonucleotide; of course, inversions can be inserted in any arbitrary number depending upon the number of "switchbacks" desired.

Thus, in one aspect, the invention is directed to "switchback" oligonucleotide sequences containing at least two tandem sequences of opposite polarities and thus at least one linkage which inverts the polarity of the oligonucleotide, and to methods of preparing and using these oligonucleotides.

The invention also comprises a method for binding a switchback oligonucleotide to portions of both strands of a double-helical polynucleotide duplex comprising the step of hybridizing the double-helical polynucleotide duplex with an oligonucleotide to form a triplex wherein the oligonucleotide is characterized by a first sequence of nucleotides capable to bind a portion of the first strand of the duplex, followed by a second sequence of nucleotides having opposite polarity capable to bind a portion on the second strand of the duplex which is proximal to said target portion on the first strand.

MODES OF CARRYING OUT THE INVENTION

Figure 1:
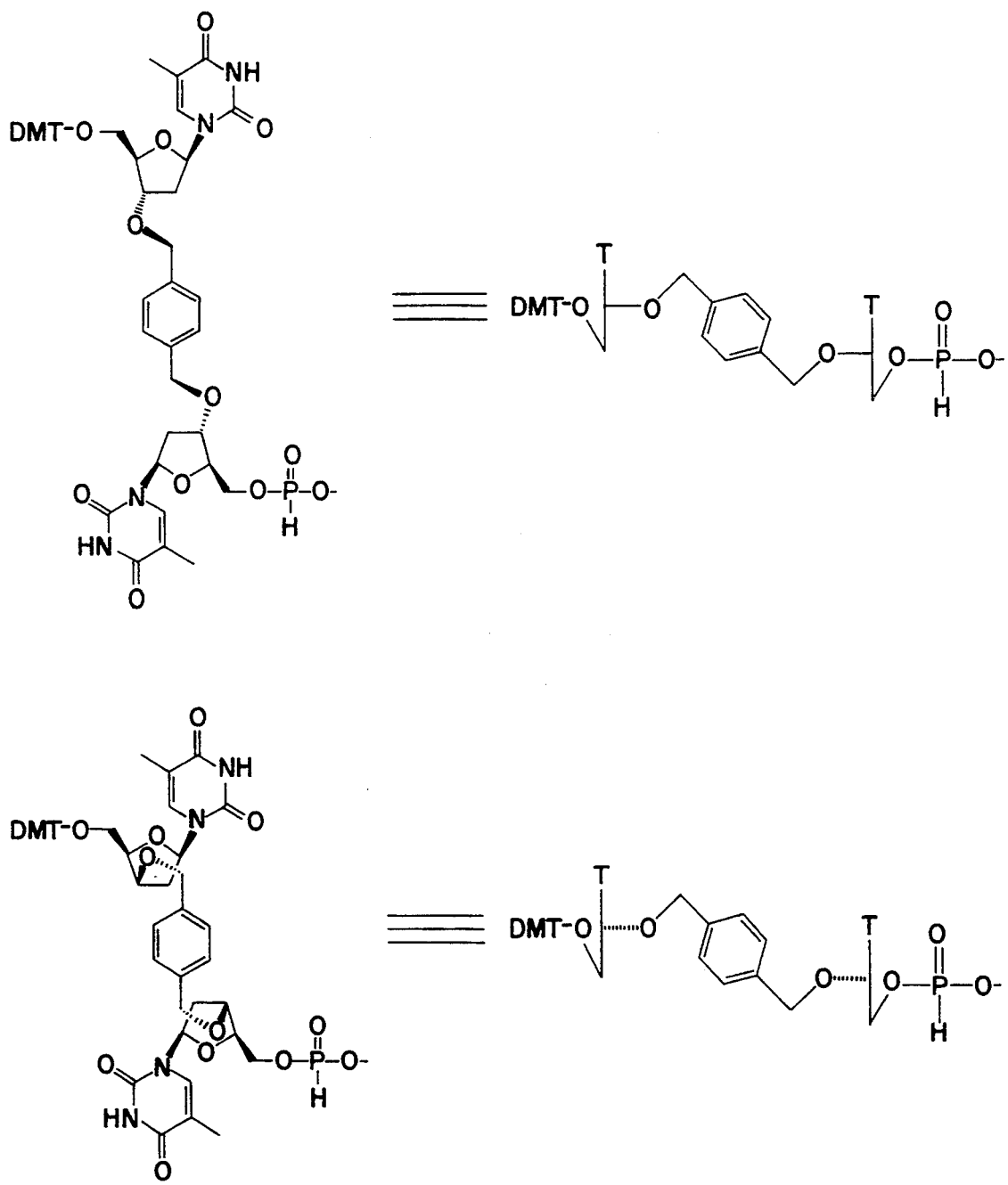
FIG. 1 shows a 1,4-dihydroxylmethylbenzene-mediated linkage between two adjacent ribosyl residues and two adjacent xylosyl residues.

As used herein "oligonucleotide" is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base. The term "nucleoside" or "nucleotide" will similarly be generic to ribonucleosides or ribonucleotides, deoxyribonucleosides or deoxyribonucleotides, or to any other nucleoside which is an N-glycoside or C-glycoside of a purine or pyrimidine base, or modified purine or pyrimidine base. Thus, the stereochemistry of the sugar carbons may be other than that of D-ribose in certain limited residues, as further described below.

"Nucleoside" and "nucleotide" include those moieties which contain not only the known purine and pyrimidine bases, but also heterocyclic bases which have been modified. Such modifications include alkylated purines or pyrimidines, acylated purines or pyrimidines, or other heterocycles. Such "analogous purines" and "analogous pyrimidines" are those generally known in the art, many of which are used as chemotherapeutic agents. An exemplary but not exhaustive list includes 4-acetylcytosine, 5-(carboxyhydroxylmethyl) uracil, 5-fluorouracil, 5-bromourcil, 5-carboxymethylaminomethyl-2-thiouracil, 5-carboxymethylaminomethyluracil, dihydrouracil, inosine, N6-isopentenyl-adenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5′methoxycarbonylmethyluracil, 5-methoxyuracil, 2-methylthio-N6-isopentenyladenine, uracil-5-oxyacetic acid methylester, uracil-5-oxyacetic acid, wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosinne, and 2,6-diaminopurine. "Nucleosides" or "nucleotides" also include those which contain modifications in the sugar moiety, for example, wherein one or more of the hydroxyl groups are replaced with halogen, aliphatic groups, or functionalized as ethers, amines, and the like. Examples of modified nucleosides or nucleotides include, but are not limited to:

| | |
|---|---|
| 2-aminoadenosine | 2′-deoxy-2-aminoadenosine |
| 5-bromouridine | 2′-deoxy-5-bromouridine |
| 5-chlorouridine | 2′-deoxy-5-chlorouridine |
| 5-fluorouridine | 2′-deoxy-5-fluorouridine |
| 5-iodouridine | 2′-deoxy-5-iodouridine |
| 5-methyluridine | (2′-deoxy-5-methyluridine is the same as thymidine) |
| inosine | 2′-deoxy-inosine |
| xanthosine | 2-deoxy-xanthosine |

Furthermore, as the α anomer binds to duplexes in a manner similar to that for the β anomers, one or more nucleotides may contain this linkage or a domain thereof. (Praseuth, D., et al, *Proc Natl Acad Sci* (USA) (1988) 85:1349–1353).

The switchback oligonucleotides of the present invention may be of any length, but lengths of greater than or equal to about 10 nucleotides, and preferably greater than about 15, are preferred. However, the longer oligonucleotides may also be made, particularly those of greater than 50 nucleotides or greater than 100 nucleotides. Oligonucleotides may contain conventional internucleotide phosphodiester linkages or may contain modified forms such as phosphoramidate linkages. These alternative linking groups include, but are not limited to embodiments wherein a moiety of the formula P(O)S, P(O)NR$_2$, P(O)R, P(O)OR′, CO, or CONR$_2$, wherein R is H (or a salt) or alkyl (1–12C) and R′ is alkyl (1–6C) is joined to adjacent nucleotides through —O— or —S—. Not all such linkages in the same oligomer need to be identical.

Inversions of polarity can also occur in "derivatives" of oligonucleotides. "Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc.). These additional moieties may be derivatized through any convenient linkage. For example, intercalators, such as acridine can be linked through any available —OH or —SH, e.g., at the terminal 5′ position of RNA or DNA, the 2′ positions of RNA, or an OH, NH$_2$, COOH or SH engineered into the 5 position of pyrimidines, e.g., instead of the 5 methyl of cytosine, a derivatized form which contains, for example, —CH$_2$CH$_2$NH$_2$, —CH$_2$CH$_2$CH$_2$OH or —CH$_2$CH$_2$CH$_2$SH in the 5 position. A wide variety of substituents can be attached, including those bound through conventional linkages. The indicated —OH moieties in the oligomers may be replaced by phosphonate groups, protected by standard protecting groups, or activated to prepare additional linkages to other nucleotides, or may be bound to the conjugated substituent. The 5′ terminal OH may be phosphorylated; the 2′—OH or OH substituents at the 3′ terminus may also be phosphorylated. The hydroxyls may also be derivatized to standard protecting groups.

The segments of 5′→3′ or 3′→5′ polarity are conventionally synthesized. Methods for such synthesis are found, for example, in Froehler, B., et al., *Nucleic Acids Research* (1986) 14:5399–5467; *Nucleic Acids Research* (1988) 16:4831–4839; *Nucleosides and Nucleotides* (1987) 6:287–291. Froehler, B., *Tet Lett* (1986) 27:5575–5578; and copending Ser. No. 248,517, filed Sep. 23, 1988, incorporated herein by reference.

In general, there are two commonly used solid phase-based approaches to the synthesis of oligonucleotides containing conventional 3′→5′ or 5′→3′ linkages, one involving intermediate phosphoramidites and the other involving intermediate phosphonate linkages. In the phosphoramidite based synthesis, a suitably protected nucleotide having a cyanoethylphosphoramidite at the position to be coupled is reacted with the free hydroxyl of a growing nucleotide chain derivatized to a solid support. The reaction yields a cyanoethylphosphite, which linkage must be oxidized to the cyanoethylphosphate at each intermediate step, since the reduced form is unstable to acid. The H-phosphonate-based synthesis is conducted by the reaction of a suitably protected nucleoside containing an H-phosphonate moiety at a position to be coupled with a solid phase-derivatized nucleotide chain having a free hydroxyl group, in the presence of a suitable activator to obtain an H-phosphonate diester linkage, which is stable to acid. Thus, the oxidation to the phosphate or thiophosphate can be conducted at any point during the synthesis of the oligonucleotide or after synthesis of the oligonucleotide is complete. The H-phosphonates can also be converted to phosphoramidate derivatives by reaction with a primary or secondary amine in the presence of carbon tetrachloride. To indicate the two approaches generically, the incoming nucleoside is regarded as having an "activated phosphite/phosphate" group.

Variations in the type of internucleotide linkage are achieved by, for example, using the methyl phosphonate precursors rather than the H-phosphonates per se, using thiol derivatives of the nucleoside moieties and generally by methods known in the art. Non-phosphorous based linkages may also be used, such as the formacetyl type linkages described and claimed in co-pending applications U.S. Ser. Nos. 426,626 and 448,914, filed on 24 October 1989 and 11 December 1989, both assigned to the same assignee and both incorporated herein by reference.

Thus, to obtain an oligonucleotide segment which has a 3′→5′ polarity, a nucleotide protected at the 5′ position and containing an activated phosphite/phosphate group at the 3′ position is reacted with the hydroxyl at the 5′ position of a nucleoside coupled to a solid support through its 3′-hydroxyl. The resulting condensed oligomer is deprotected and the reaction repeated with an additional 5′-protected, 3-′phosphite/phosphate activated nucleotide. Conversely, to obtain an oligomeric segment of 5'→3' polarity a nucleotide protected in the 3' position and containing an activated phosphite/phosphate in the 5' position is reacted with a nucleotide oligomer or nucleoside attached to a solid support through the 5' position, leaving the 3'-hydroxyl available to react. Similarly, after condensation of the incoming nucleotide, the 3' group is deprotected and reacted with an additional 3'-protected, 5'-activated nucleotide. The sequence is continued until the desired number of nucleotides have been added.

In addition to employing these very convenient and now most commonly used, solid phase synthesis techniques, oligonucleotides may also be synthesized using solution phase methods such as triester synthesis. These methods are workable, but in general, less efficient for oligonucleotides of any substantial length.

In their most general form, the inverted polarity oligonucleotides of the invention contain at least one segment along their length of the formula:

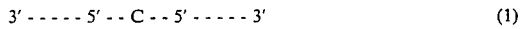   (1)

or

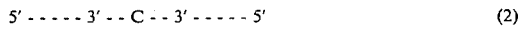   (2)

where —C— symbolizes any method of coupling the nucleotide sequences of opposite polarity.

In these formulas, the symbol 3'- - - 5' indicates a stretch of oligomer in which the linkages are consistently formed between the 5' hydroxyl of the ribosyl residue of the nucleotide to the left with the 3' hydroxyl of the ribosyl residue of the nucleotide to the right, thus leaving the 5' hydroxyl of the rightmost nucleotide ribosyl residue free for additional conjugation. Analogously, 5'- - - 3' indicates a stretch of oligomer in the opposite orientation wherein the linkages are formed between the 3' hydroxyl of the ribosyl residue of the left nucleotide and the 5' hydroxyl of the ribosyl residue of the nucleotide on the right, thus leaving the 3' hydroxyl of the rightmost nucleotide ribosyl residue free for additional conjugation.

The linkage, symbolized by —C—, may be formed so as to link the 5' hydroxyls of the adjacent ribosyl residues in formula (1) or the 3' hydroxyls of the adjacent ribosyl residues in formula (2), or the "—C—" linkage may conjugate other portions of the adjacent nucleotides so as to link the inverted polarity strands. "—C—" may represent a linker moiety, or simply a covalent bond.

It should be noted that if the linkage between strands of inverted polarity involves a sugar residue, either the 3' or 2' position can be involved in the linkage, and either of these positions may be in either R or S configuration. The choice of configuration will in part determine the geometry of the oligomer in the vicinity of the linkage. Thus, for example, if adjacent 3' positions are used to effect a covalent linkage, less severe deformation of the oligonucleotide chain will generally occur if both 3' hydroxyls involved in the linkage are in the conventional R configuration. If they are both in the S configuration, this will result in a "kink" in the chain.

In addition to the use of standard oligonucleotide synthesis techniques or other couplings to effect the 5'—5' or 3'—3' linkage between ribosyl moieties, alternative approaches to joining the two strands of inverted polarity may be employed. For example, the two appended bases of the opposing termini of the inverted polarity oligonucleotide sequences can be linked directly or through a linker, or the base of one can be linked to the sugar moiety of the other. Any suitable method of effecting the linkage may be employed. The characterizing aspect of the switchback oligonucleotides of the invention is that they comprise tandem regions of inverted polarity, so that a region of 3'→5' polarity is followed by one of 5'→3' polarity, or vice versa, or both.

Depending on the manner of coupling the segments with inverted polarity, this coupling may be effected by insertion of a dimeric nucleotide wherein the appropriate 3' positions of each member of the dimer or the 5' positions of each member of the dimer are activated for inclusion of the dimer in the growing chain, or the conventional synthesis can be continued but using for the condensing nucleotide a nucleotide which is protected/activated in the inverse manner to that which would be employed if the polarity of the chain were to remain the same. This additional nucleotide may also contain a linker moiety which may be included before or after condensation to extend the chain.

For example, in one illustrative embodiment of the formulas (1) and (2), these compounds include inversion-conferring linkages of the formulas:

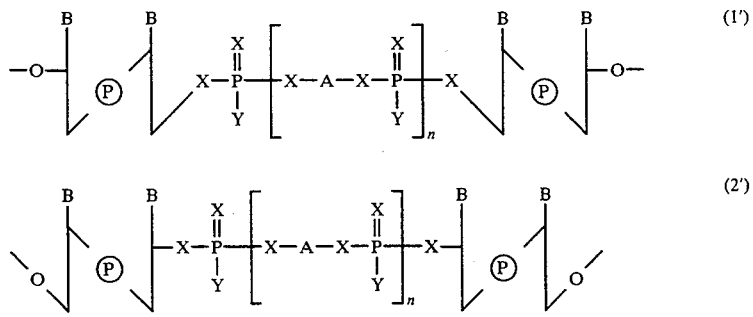

or the more complete representation:

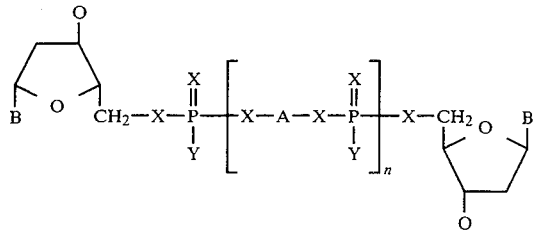

(1')

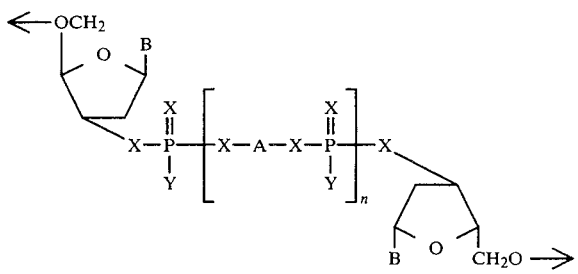

(2')

wherein:

B is any purine or pyrimidine base, modified purine or pyrimidine base, or any desired corresponding moiety of an analogous nucleotide and (P) represents a phosphodiester linkage or a conventional substitute therefor, such as methyl phosphonate;

Y is H, —OR, —SR, —NR$_2$, O$^-$, or S$^-$;

X is O, S, or NR;

wherein each R is independently H, alkyl (1–12C), aryl(6–12C), aralkyl(7–20C) or alkaryl(7–20C);

n is 0 or 1; and

A is the residue of a linker group.

Thus, in these representations, the bold line refers to the sugar, whereas B represents the bases. The (P) within the diagonal line in the diagram denotes a phosphodiester or analogous bond. This diagonal line joins the end of one bold line and the middle of another. These junctions refer to the 5'—OH and 3'—OH, respectively.

This type of linkage is convenient because —C— can be incorporated sequentially using the standard solid phase synthesis techniques. Although shown specifically to effect a 5'—5' or 3'—3' linkage, the linking portion per se can be used to couple sugar-sugar, sugar-base or base-base on adjacent switchback nucleotide residues. Also, any linkage form can be included using a prelinked dimer in the solid phase sequence.

When n is 0 in the above embodiment, the 3'—3' or 5'—5' linkage is simply formed using standard oligonucleotide synthesis techniques wherein the nucleotide to be added to the sequence is protected and activated in the opposite orientation from that which would be used if the original chain polarity were followed. When n=1, a linker is utilized to effect the inverted polarity linkage. There is no theoretical reason that n cannot be >1; however, generally it is more convenient to limit the synthesis to the intermediation of one linker.

When a linker moiety is employed, the phosphite/phosphate activated linker can be included directly in the continuing oligonucleotide synthesis, followed by coupling to the first nucleotide of the inverted sequence or the first such nucleotide can be supplied already derivatized to the phosphite/phosphate activated linker. In general, the linker comprises a diol or diamine, the residue of which appears as "A" in formulas 1' and 2'. Thus, in a typical synthesis protocol, one hydroxyl (or amino) of the diol (or diamine) is protected and the other is an activated phosphite/phosphate. This protected form can be coupled to the oligonucleotide chain attached to the solid support and then deprotected and reacted with the subsequent nucleotide residue.

Similar diol or diamine type (or disulfhydryl or hydroxyl/sulfhydryl type) linkers are also convenient when the linkage between inverted polarity segments is to be effected between adjacent bases or between a base and a sugar moiety, or these can be used to link adjacent sugars directly without the inclusion of the phosphodiester or analog thereof. In these instances, it is generally more convenient to synthesize the switchback nucleotide dimer independently, and then to insert the dimer, again using standard oligonucleotide synthesis techniques, into the oligonucleotide to be formed. Alternate linker functionalities can be convenient when adjacent base moieties are to be used, however, in general, convenient forms of linkers are those derived from dihydroxy, diamino (or disulfhydryl or hydroxyl/sulfhydryl) compounds which can be suitably protected and activated so as to integrate them into the standard oligonucleotide synthesis protocol or otherwise used to obtain inverted dimeric nucleotides.

The significant step in the integration of these linkers, however, is that the subsequent additions to the oligomer, after the linker is inserted, are activated and deprotected nucleotides having opposite polarity from that of the preceding portion of the sequence.

Thus, illustrative suitable linkers are or include residues of diols of the following formulas or their analogous diamines (or alcohol amines). For ease of representation, the diol structures are used, but it should be kept in mind that either or both hydroxyl functionality may be replaced by an amino group or a sulfhydryl group.

HO(CH$_2$)$_{n1}$OH, wherein n1 is an integer that is usually 1–15, but can also be in an extended form. One or more of the —CH$_2$— groups may be replaced by O, S or NH, provided such replacement is not adjacent to a heteroatom. (When integrated into formula 1' or 2', therefore, this linker will give "A" as a residue of the formula —(CH$_2$)$_{n1}$—).

In particular, the diol may represent a polyethylene glycol of the formula $HO(CH_2CH_2O)_{n2}H$, wherein $n2$ is an integer of 1–5.

The linker may also contain unsaturation, so that it may be of the exemplary formulas:

$HOCH_2(CX_2CX_2)_{n3}CH_2OH$, wherein $n3$ is an integer of 1–7 and each pair of X or adjacent C is independently H or a $\pi$ bond; or $HOCH_2(CX_2CX_2)_{n4}CH_2(CX_2CX_2)_{n5}CH_2OH$, wherein $n4$ and $n5$ are integers of 0–7 and wherein the sum of $n4$ and $n5$ is not greater than 7 and wherein each pair of X or an adjacent C is independently H or together are a $\pi$ bond.

In these embodiments also, one or more methylene groups may be replaced, provided it is not adjacent to an additional heteroatom, by O, S or NH.

The dihydroxy, diamino or equivalent linker compound may also be cyclic, either non aromatic or aromatic. Nonaromatic embodiments include diols such as cis- or trans-3-4-dihydroxyfuran, cis- or trans-2-hydroxymethyl-3-hydroxyfuran, and cis- or trans-2-hydroxymethyl-4-hydroxyfuran, said furan either further unsubstituted, or further substituted with one or two non-interfering alkyl(1–4C) substituents, or may include N-heterocycles such as piperazine or piperidine.

Linkers containing aromatic rings may include residues of 1,2-dihydroxymethylbenzene; 1,4-dihydroxymethylbenzene; 1,3-dihydroxymethylbenzene; 2,6-dihydroxy methylnaphthalene; 1,5-dihydroxymethylnaphthalene; 1,4-bis(3-hydroxypropenyl)benzene; 1,3-bis(3-hydroxy propenyl)benzene; 1,2-bis(3-hydroxypropenyl)benzene; 2,6-bis(3- hydroxypropenyl)naphthalene; 1,5-bis(3-hydroxypropenyl)naphthalene, 1,4-bis (3-hydroxy propynyl)benzene; 1,3-bis(3-hydroxypropynyl)benzene; 1,2-bis(3-hydroxypropynyl) benzene; 2,6-bis(3-hydroxypropynyl)naphthalene; and 1,5-bis(3-hydroxypropynyl)naphthalene. FIG. 1 shows the coupling using 1,4-dihydroxymethylbenzene as it bridges either two ribosyl or two xylosyl residues.

In addition, the linker may carry additional functional groups, such as anthraquinone and be fairly complex; an example of this type of linker is:

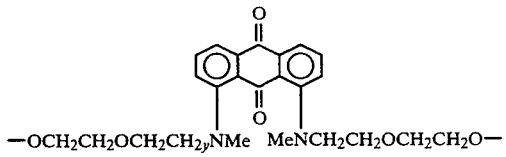

$-OCH_2CH_2OCH_2CH_2)_yNMe$   $MeNCH_2CH_2OCH_2CH_2O-$

The length and type of internucleotide linkage at the inverted junction will depend in part on the charge concentration (e.g., polyphosphodiester groups may be too highly concentrated in charge) and on the distance required to span the major groove in the duplex in order to achieve the required triple helix binding. It is presently considered that spanning the two strands of the duplex through a 5'—5' switchback involves no null bases, while a 3'—3' switchback involves 1–4 null bases in the duplex target. In general, the oligomer spacing accounts for 0–4 null bases, depending on the embodiment. (A "null" base refers to a base pair in the DNA duplex that does not hydrogen bond to the third strand moiety.) The length of the linker can be adjusted accordingly. The proper length and type of linkage may be determined by those of ordinary skill in the art using routine optimization procedures.

Synthesis Methods

For the embodiments of formulas 1' and 2', the synthesis of oligonucleotides having inverted polarity may be accomplished utilizing standard solid phase synthesis methods.

This oligonucleotide chain elongation will proceed in conformance with a predetermined sequence in a series of condensations, each one of which results in the addition of another nucleotide. Prior to the addition of a nucleoside having an activated phosphite/phosphate, the protecting group on the solid support-bound nucleotide is removed. Typically, for example, removal of the commonly-employed dimethoxytrityl (DMT) group is done by treatment with 2.5% v/v dichloroacetic acid/dichloromethane, although 1% w/v trichloroacetic acid/dichloromethane or $ZnBr_2$-saturated nitromethane, are also useful. Other deprotection procedures suitable for other protecting groups will be apparent to those of ordinary skill in the art. The deprotected nucleoside or oligonucleotide bound to solid support is then reacted with the suitably protected nucleotide containing an activated phosphite/phosphate. After each cycle the carrier-bound nucleotide is preferably washed with anhydrous pyridine/acetonitrile (1:1, v/v), again deprotected, and the condensation reaction is completed in as many cycles as are required to form the desired number of congruent polarity internucleotide bonds which will be converted to phosphoramidates, phosphorodithioates, phosphorothioates or phosphodiesters as desired.

In one embodiment, to provide the switchback, the incoming activated, protected nucleoside is provided in the opposite polarity to the support-bound oligomers. Thus, for example, where the support-bound oligomer is 3'→5', the deprotected 5' hydroxyl is reacted with a 3'-protected, 5'-activated monomer, and the synthesis continued with monomers activated at the 5' position and protected at the 3' position.

In another embodiment, to provide a linker in the switchback, a molecule having one end which is activated for condensation (such as a hydrogen phosphonate) to the support-bound oligonucleotide and another end which is a protected hydroxyl group (or protected thio group) is condensed onto the support-bound oligonucleotide. The linker group is condensed and deprotected using the same conditions as those used to condense and deprotect the protected nucleoside hydrogen phosphonate. Subsequent extension of the oligonucleotide chain then uses oligonucleotide residues which are activated and protected in the opposite manner from those used to synthesize the previous portion of the chain.

If coupling of the inverted portion of the oligonucleotide is through an internucleotide linkage conjugating the bases of adjacent nucleotides or the base of one nucleotide to the ribosyl moiety of the other, or adjacent ribosyl residues through linkages which do not involve activated phosphite/phosphate, it is preferable to form the dimeric nucleotide, which is then included in the synthesis in suitably activated and protected form. For example, adjacent methyl cytosines or thymidines may be linked through the methyl groups at the 5-positions of the pyrimidine rings using a variety of techniques by converting the 5-position to, for example, hydroxymethyl, allyl amine, acrylic acid, or propenyl residues, as is commonly practiced. These reactive groups can then be further coupled through bifunctional linkers or by suitable alternate condensation to obtain dimeric forms of the methyl cytidine or thymidine, or mixed nucleosides. For inclusion of the dimer in the oligonucleotide of inverted polarity, the dimer is protected, if needed, in, for example, both 5' positions and activated in one 3' position and protected in the other for continuation of the synthesis. Extension of the chain continues from the included dimer using nucleosides of inverted protection/activation patterns.

One series of reactions, resulting in linkage of the 3' positions in adjacent xylosyl residues through 1,4-dimethoxybenzene is shown in Reaction Scheme 1.

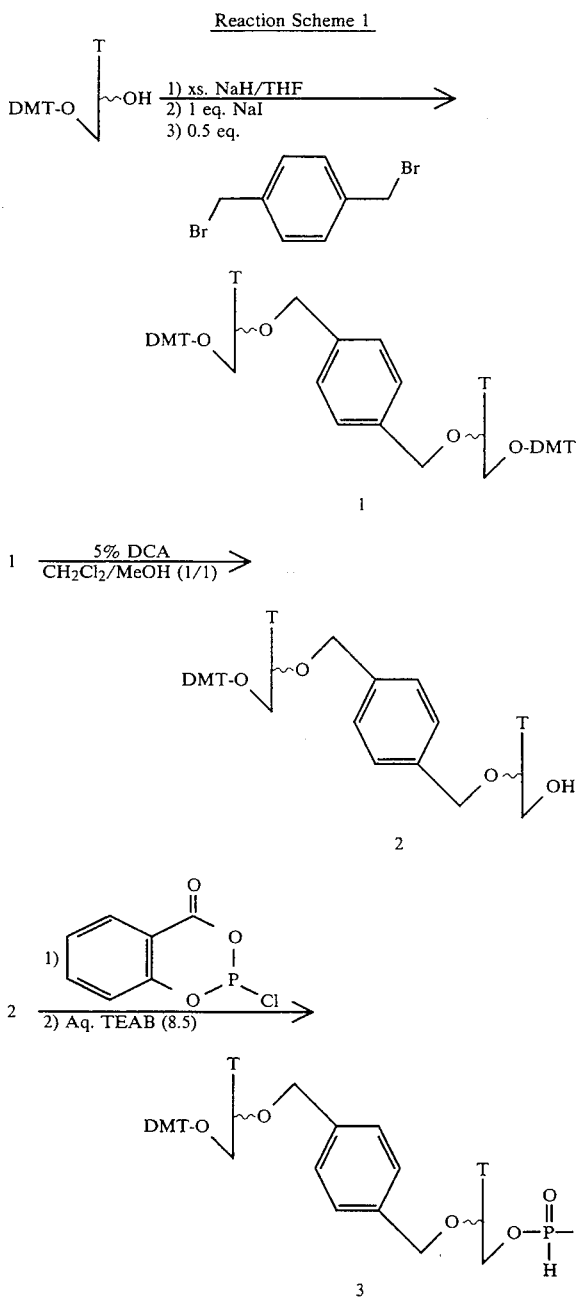

Figure 2:
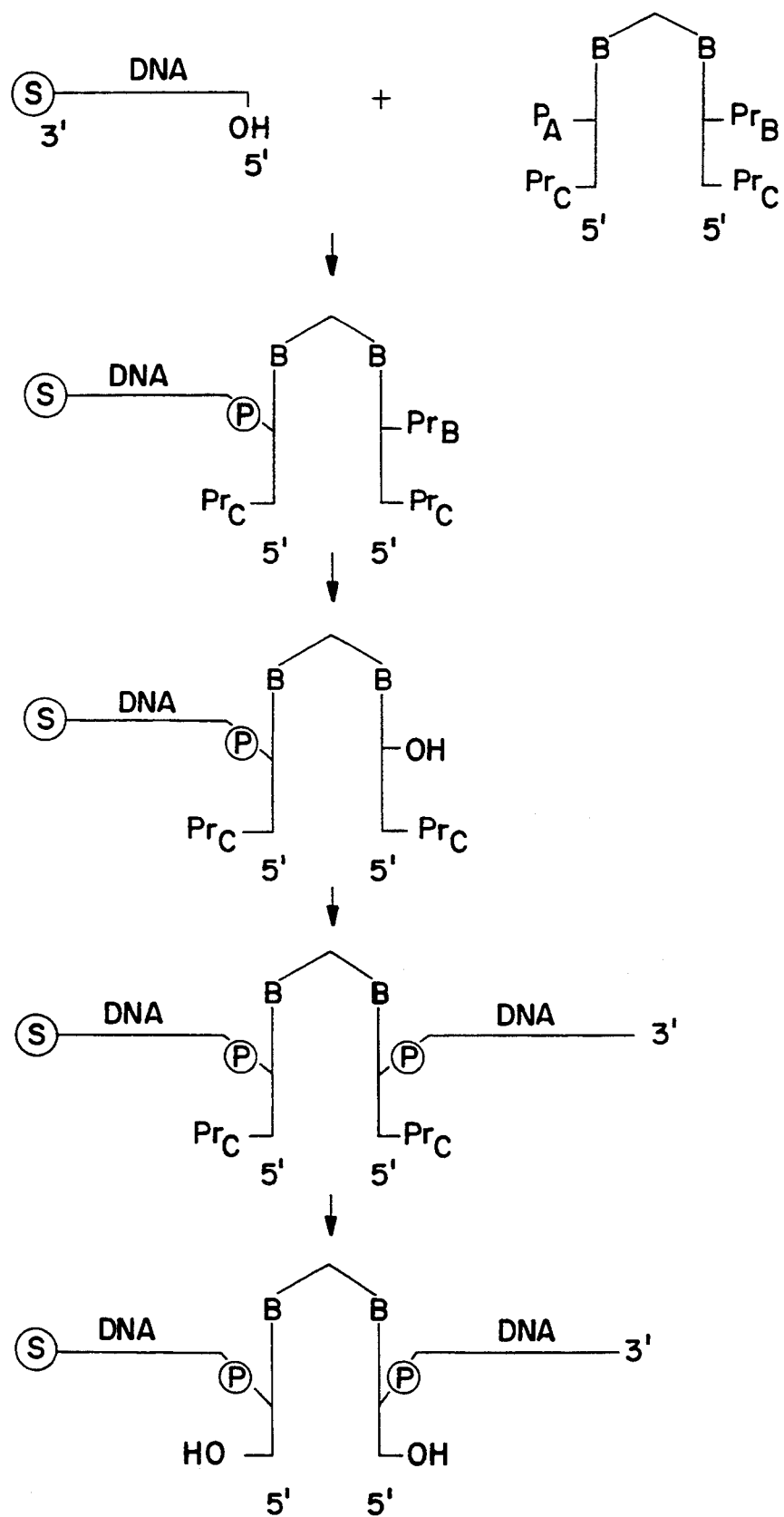
FIG. 2 shows an outline of the reaction scheme to include a dimer synthon in the oligomer to obtain a switchback.

In another example, for a dimer wherein adjacent 5-positions of the bases are linked through —(CH= CH—CH$_2$NH)$_2$CO, the inclusion of this dimer to obtain a 5'—5' link can be shown diagrammatically in FIG. 2 where $\text{\textcircled{S}}$= polymeric or other solid phase support, Pr$_B$=a DMT protecting group; Pr$_C$ is a trimethyl acetyl protecting group; P$_A$=activated phosphite/phosphate; and $\text{\textcircled{P}}$ is as defined above.

Dimers may also be formed between adjacent sugars, and the resulting dimers used as above in standard synthesis. For example, the 3' positions of two ribosyl, xylosyl or ribosyl/xylosyl moieties on adjacent nucleotides may be linked through a p-dihydroxymethyl benzene or other linker such as 1,3-propylene glycol or ddR of the formula:

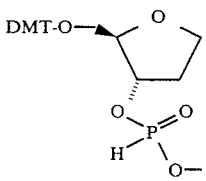

and the 5' positions of the dimer used in subsequent synthesis. (For these latter two linkers, standard incorporation into the oligomer synthesis scheme can also be used.) In this case one 5'-position is protected with a DMT and the other is activated phosphite/phosphate. Conversely, for adjacent sugars linked through the 5' position, one 3'-position is protected and the other activated. As stated above, the geometry of the oligonucleotide at the linkage site will be affected by the chirality of the 3' carbons involved in the linkage.

As stated above, all of the internucleotide linkages in the resulting oligomer need not be identical. By use of appropriate synthesis techniques, some can be phosphodiesters, some phosphonates, some phosphoramidates, etc.

As set forth above, the inverted polarity oligonucleotides of this invention may be derivatized. One convenient method to form such derivatization is through the phosphoramidate linkage. The amine which is utilized to form the phosphoramidate may employ substituents that can confer useful properties to the oligonucleotide. For example, if an amine linked to a polyethylene glycol, a polypeptide or a lipophilic group is utilized, such a group may facilitate transport of the oligonucleotide through the cell membranes, thus increasing the cellular uptake of the oligonucleotide. A substituent on the amine may also include a group which affects the target DNA to which the oligonucleotide will bind such as providing covalent linkages to the target strand to facilitate cleavage or intercalation of the switchback oligonucleotide to the target strand. The substituents on the amine may contain chromophoric groups such as fluorescein or other labels, including radioactive labels, chelating agents and metal chelated ions, to label the oligonucleotide for identification. The substituents may thus also serve a cutting function (i.e., a site for cutting the duplex) or a receptor function such as a receptor ligand. The substituents on the amine which form the phosphoramidate linkage may thus be virtually any moiety which does not prevent the oligonucleotide from binding to the target duplex.

More than one derivatizing moiety may also be used as two or more phosphoramidate linkages need not contain the same substituents. This may be accomplished by generating a first nucleotide hydrogen phosphonate linkage and then oxidizing it with a first amine, generating a second hydrogen phosphonate linkage and oxidizing it with a second (different) amine.

While the formation of the phosphoramidate linkage provides a convenient method for attaching the groups which derivatize the oligonucleotide to confer useful properties, other methods may also be used. The useful substituents may be attached to the sugar moieties or to the bases, or by any other method generally known in the art.

After completion of the synthesis, the oligonucleotide is separated from the carrier using conventional methods, such as, by incubation with concentrated ammonium hydroxide. Any protecting groups (for example, on the purine or pyrimidine bases) may be removed using, for example, the conventional concentrated ammonia reagent. The oligonucleotide is then purified by conventional means such as HPLC, PAGE (polyacrylamide gel electrophoresis) or any other conventional technique.

It will be understood that while the above method has been described in connection with use of a solid state carrier, it is also possible to conduct the synthesis without the use of a solid state support. In such an event, in place of the support a 3'-hydroxy protecting group which is different from the 5' protecting group used in the course of the condensation, may be utilized so that the 5' protecting group may be selectively removed while the 3' protecting group remains intact.

Binding Properties

The oligonucleotides with inverted polarity according to the present invention are useful to bind to a double-helical nucleotide duplex to form a triplex. The conditions for hybridization to form a triplex are known, as shown for example by Moser and Dervan, supra. Hybridization normally takes place at a pH in the range of about 6-7. The nucleotides according to the present invention will comprise, on one side of the 3'—3' (or 5'—5') inversion, bases which bind to one strand of the duplex according to the triple helix code, with the bases on the other side of the 3'—3' (or 5'—5') junction selected to be bases which will bind according to this code to the subsequent bases on the opposite strand of the duplex.

In this manner triple helix recognition may be extended by switching recognition from one strand of the duplex to the other and then back again, if desired. Also, certain nucleases may be blocked, since the oligonucleotides according to the present invention can present ends not recognizable by exonucleases. Thus, oligonucleotides having two 5'-ends, will be resistant to 3'-exonucleases.

Since the switchback oligonucleotides of the invention are intended to expand the strength of binding to duplex DNA, the sequence of nucleotides in each portion of the oligonucleotide is determined by the sequence of bases in the target duplex. Target duplex sequences which contain multiple adenyl residues in a homopurine region of one chain, followed by a region of homopurines comprising guanines in the opposite strand will mandate a switchback oligonucleotide which is polyT in the polarity opposite to the polyA tract followed by polyC in the polarity opposite to that of the polyG tract, assuming antiparallel binding. Alternating A/G sequences in the first strand of the target duplex will mandate alternating T/C sequences in a first region of congruent polarity (same sense) in the switchback oligonucleotide followed by a sequence of inverted polarity which matches the second strand sequential sequence in the duplex, again assuming antiparallel binding. As the switchback oligonucleotide is intended for complexing to form a triple helix, it is generally comprised mainly of pyrimidine-based nucleotides. However, it is also known that the geometry of the double helix results in a spacing requirement so that at a 3'—3' linkage there will be approximately 0-4 essentially null bases in the oligonucleotide; there appear to be no null bases required in the 5'—5' switchback. The null base spacing can be provided by arbitrary nucleotide insertions or, alternatively, the length of a linker moiety may be adjusted to compensate for this.

In addition to enhanced capability to bind to the duplex by formation of a triplex through the switchback in the oligonucleotide of the invention, these oligonucleotides may also form D-loops with the duplex. In this situation, the region of a first polarity may, for example, form a triplex, while the inverted portion displaces a section of one strand of the duplex to result in a substitute duplex in the relevant region. The design of the sequence of bases in the oligonucleotide takes account of this by utilization of a sequence which is designed to base pair hybridize to the target strand.

In summary, the switchbacks may bind the duplexes in a variety of conformations including both antiparallel and parallel binding modes, direct crossovers of the form

switchback modes of the form

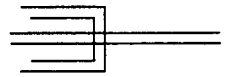

or D-loops.

Utility and Administration

As the switchback oligonucleotides of the invention are capable of significant duplex binding activity, these oligonucleotides are useful in oligonucleotide therapy. Oligonucleotide therapy is a generic term which includes the use of specific binding oligonucleotides to inactivate undesirable DNA or RNA sequences in vitro or in vivo. Because of their superior binding ability to duplex DNA, the switchback oligonucleotides are particularly helpful in this regard.

Most diseases and other conditions are characterized by the presence of undesired DNA or RNA, some of which may be in duplex form. These diseases and conditions can be treated using the principles of oligonucleotide therapy as is generally understood in the art. Oligonucleotide therapy includes targeting a specific DNA or RNA sequence through complementarity or through any other specific binding means, in the case of the present invention by sequence-specific orientation in the major groove of the DNA double helix.

In addition to oligonucleotide therapy applications, wherein specific sequence recognition is significant, alternate therapeutic mechanisms for the switchback oligomers of the invention can be advantageously employed. Such oligomers are generally useful as inhibitors of polymerases such as viral polymerases, to interfere with binding factors to nucleic acids such as transcription initiating or inhibiting factors, to induce the production of interferon endogenously, and so forth. The oligomers of the invention may be administered singly, or combinations of oligomers may be administered for adjacent or distant targets or for combined effects of antisense mechanisms with the foregoing general mechanisms.

In therapeutic applications, the switchback oligomers are utilized in a manner appropriate for antisense therapy in general or to take advantage of the alternate therapeutic mechanisms set forth above. For such therapy, the oligomers can be formulated for a variety of modes of administration, including systemic, topical or localized administration. Techniques and formulations generally may be found in *Remington's Pharmaceutical Sciences,* Mack Publishing Co., Easton, Penna., latest edition. The oligomer active ingredient is generally combined with a carrier such as a diluent or excipient which may include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile sales and fusidic acid derivatives for transmucosal administration. In addition, detergents may be used to facilitate permeation. Transmucosal administration may be through use of nasal sprays, for example, or suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

In addition to use in therapy, the oligomers of the invention may be used as diagnostic reagents to detect the presence or absence of the target DNA or RNA sequences to which they specifically bind. Such diagnostic tests are conducted by hybridization through triple helix formation which is then detected by conventional means. For example, the oligomers may be labeled using radioactive, fluorescent, or chromogenic labels and the presence of label bound to solid support detected. Alternatively, the presence of a triple helix may be detected by antibodies which specifically recognize these forms. Means for conducting assays using such oligomers as probes are generally known.

In addition to the foregoing uses, the ability of the oligomers to inhibit gene expression can be verified in in vitro systems by measuring the levels of expression in recombinant systems.

The following examples are provided to illustrate but not to limit the invention.

EXAMPLE 1

Preparation of 3'-DMT-$N^4$-benzoyl-dC-5'-H-phosphonate 6.4 g (1C mmole) of 5'-DMT $N^4$-benzoyl deoxy-C is dried from 100 ml of pyridine, dissolved into 100 ml of pyridine and to this is added 4 g (11.8 mmole) of DMT-Cl and the reaction mixture stirred at room temperature for three days.. The reaction mixture is evaporated to approximately half the volume and diluted with 100 ml of $CH_2Cl_2$, wash with 5% sodium bicarbonate ($2 \times 100$ ml), dry over sodium sulfate and evaporate to dryness. The crude mixture is dissolved into 100 ml of toluene and evaporated to a foam, and this is repeated one more time. The solid is taken up in 50 ml of diethyl ether/50 ml of $CH_2Cl_2$ and precipitated into 900 ml of hexane at room temperature. The solid is isolated and dissolved into 15 ml of $CH_2Cl_2$, cool to 0° C. and add 100 ml of saturated $ZnBr_2$ in isopropanol/$CH_2Cl_2$ (15/85) and stirred for 15 minutes. Reaction mixture is quenched into 400 ml of 1M $NH_4$ OAc, the organic layer separated and wash with $NaHCO_3$ ($1 \times 200$ ml), dry over $Na_2SO_4$ and evaporate. Purify by silica gel chromatography ($CH_2Cl_2$/5% MeOH) to yield 50% of the 5'—OH product. The 5'—OH nucleoside is dried from 50 ml of pyridine then taken up in 10 ml pyridine and 10 ml of methylene chloride, to which is added 2 eq. of 1M PA/$CH_2Cl_2$ in 5 ml of pyridine. This mixture is stirred at r.t. for 15 minutes and quenched into 1M TEAB, the layers are separated, and the organic layer is washed with TEAB (1 time), dried over sodium sulfate and evaporated to dryness. The reagent PA is yon Boom's Reagent, 2-chloro-4H-1,3,2-benzodioxaphosphorin-4-one. The nucleoside H-phosphonate is purified by silica gel chromatography (1% triethylamine/$CH_2Cl_2$) with a MeOH gradient.

EXAMPLE 2

Preparation of 3'-DMT-thymidine-5'-H-phosphonate 1.2 g (5 mmole) of thymidine is dried from 50 ml of pyridine, taken up in 20 ml of pyridine and under Ar is added 820 mg (5.5 mmole) of t-butyldimethyl silyl chloride in 5 ml of pyridine. The mixture is stirred at room temperature for one day, concentrated to approximately 10 ml, diluted with 75 ml of $CH_2Cl_2$, washed with 5% $NaHCO_3$, back extracted the aqueous with $CH_2Cl_2$, dried over $Na_2SO_4$ and evaporated. The crude nucleoside is dried from 20 ml pyridine, taken up in 30 ml pyridine and to it is added 1.7 g (5 mmole) of DMT-Cl and 0.4 ml of triethylamine, after which the mixture is stirred for three days. After evaporation to approximately 10 ml, the mixture is diluted with 75 ml of $CH_2Cl_2$ and washed with $NaHCO_3$ ($2 \times 100$ ml), dried over $Na_2SO_4$ and evaporated. The 5'—OH nucleoside is taken up into 60 ml THF and 20 ml of 1M TBAF/THF is added. After stirring for one hour, the mixture is evaporated to an oil, taken up in $CH_2Cl_2$ and applied to silica gel column. Yield 50%. The 5'—OH nucleoside is then converted to H-phosphonate as in Example 1.

EXAMPLE 3

Synthesis of Oligomer-Containing Switchbacks

Polynucleotide H-phosphonates condensed at the 3'-end to a solid polymer support are prepared as described by Froehler, et al., *Nuc Acids Res* 16:4831–4839 (1988); *Nuc Acids Res* 14:5399–5467 (1986); and *Nucleosides and Nucleotides* 6:287–291 (1987); using the DBU salt of 5′-protected nucleoside H-phosphonates. After four couplings, one coupling cycle is performed using the ethylene glycol derivative:

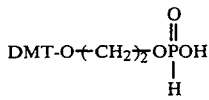

The polynucleotide H-phosphonate is then oxidized with aqueous $I_2$ (0.1M in N-methyl morpholine/water/THF, 5/5/90) to form internucleotide diester linkages. Then five coupling cycles are performed using 3′-protected nucleoside 5′-H-phosphonates, prepared as in Examples 1 and 2. After these couplings the remaining H-phosphonate linkages on the polynucleoside are oxidized with 2-methoxyethylamine in Pyr/CCl$_4$ (1/5/5), to generate a 10-mer with five diester linkages (one of which is with the ethylene glycol linker) and five phosphoramidate linkages (one of which is with the ethylene glycol linker). The oligomer is removed from the solid support, deprotected with concentrated NH$_4$OH, purified by HPLC (PRP) using an acetonitrile gradient in 50 mM aqueous TEAP. DMT is removed using 80% HOAc (R.T.) and the solvent is evaporated. The product is desalted, and isolated by evaporation.

Thus, in this manner the following are prepared, wherein $P_1$ represents

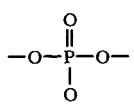

(having an ionization state determined by pH):

```
3'              5'              5'              3'
C—C—C—C—C—P1—CH2CH2—P1—C—C—C—C—C

3'              5'              5'              3'
C—T—C—T—C—P1—CH2CH2—P1—C—T—C—T—C

3'              5'              5'              3'
T—T—C—C—C—P1—CH2CH2—P1—C—C—C—T—T

3'              5'              5'              3'
T—C—T—T—T—P1—CH2CH2—P1—C—T—T—C—T
```

By utilizing nucleosides derivatized to solid support through the 5′ portion and extending the chain with the 3′-protected, 5′-activated nucleosides of Examples 1 and 2, followed by coupling to DMT—O—CH$_2$CH$_2$—P$_1$ as above, followed by chain extension, with conventional 5′-protected, 3′-activated nucleosides, the following are prepared.

```
5'              3'              3'              5'
C—C—C—C—C—P1—CH2CH2—P1—C—C—C—C—C

5'              3'              3'              5'
C—T—C—T—C—P1—CH2CH2—P1—C—T—C—T—C

5'              3'              3'              5'
T—T—C—C—C—P1—CH2CH2—P1—C—C—C—T—T

5'              3'              3'              5'
T—C—T—T—T—P1—CH2CH2—P1—C—T—T—C—T
```

By insertion of an additional linker, the following are prepared:

```
3'              5'              5'              3'              3'              5'
C—C—C—C—C—P1—CH2CH2—P1—C—C—C—C—C—P1—CH2CH2—P1—C—C—C—C—C

3'              5'              5'              3'              3'              5'
C—T—C—T—C—P1—CH2CH2—P1—C—T—C—T—C—P1—CH2CH2—P1—C—T—C—T—C

3'              5'              5'              3'              3'              5'
T—T—C—C—C—P1—CH2CH2—P1—T—T—C—C—C—P1—CH2CH2—P1—C—C—C—T—T

3'              5'              5'              3'              3'              5'
T—C—T—T—T—P1—CH2CH2—P1—T—C—T—T—T—P1—CH2CH2—P1—C—T—T—C—T.
```

EXAMPLE 4

Synthesis and Assay of a Recognition Switchback

Using the methods of Example 3, a switchback 24-mer linked with propylene glycol was prepared of the formula:

```
5'  TCTTTCTTTTCTT      TTCTTCTTTTT  5'
                   3'  3'
                   Linker
```

The duplex DNA to which this oligomer binds has a 26-bp target region having 2 null bases to accommodate the switchback. This target region is of the formula:

```
5'  AGAAAGAAAAGAAATTTCTTCTTTTT  3'
3'  TCTTTCTTTTCTTTAAAGAAGAAAAA  5'
```

To assess the capacity of the switchback oligomer to bind the target region, an assay was conducted as follows. A 144-bp fragment containing four 36-bp cassettes, one of which corresponds to the desired target region, was cloned into pTZ18U, a commercially available cloning vector. The plasmid was cleaved and labeled at both ends with 32 PdCTP, and then digested with a second restriction enzyme to eliminate the label at one end and reduce the size of target DNA. The resulting 372 bp fragment was purified using 5% acrylamide gel.

The switchback oligomer (1 μmol) was incubated with $5 \times 10^4$ cpm labeled target in 100 mM NaCl, 10 mM MgCl$_2$, 50 mM MES, pH 6, at room temperature for one hour.

The reaction mixtures were then treated with 0.5 μg/ml DNAse-I for 1 minute at room temperature, and extracted to terminate the digestion and remove protein. The DNA was recovered by ethanol precipitation, and the samples were loaded onto 8% polyacrylamide gel in 80% formamide and run under denaturing conditions for 2 hours at 60 watts. The gel was dried and placed on film overnight. The results showed that the oligomer provided protection against DNAse-I activity

I claim:

1. An oligonucleotide comprising
   a first nucleotide sequence containing at least three nucleotide residues, said sequence having either 3'→5' or 5'→3' polarity, and, coupled thereto,
   a second nucleotide sequence containing at least three nucleotide residues, said second sequence having polarity inverted from that of the first sequence.

2. The oligonucleotide of claim 1 wherein
   the 5' position of a nucleotide at the 5' end of the first sequence is covalently bonded to the 5' position of the nucleotide at the 5' end of the second sequence, or wherein
   the 3' position of a nucleotide at the 3' end of the first sequence is covalently bonded to the 3' position of the nucleotide at the 3' end of the second sequence.

3. The oligonucleotide of claim 1 wherein
   the base of the nucleotide at the 5' end of the first sequence is covalently bonded to the base of the nucleotide at the 5' end of the second sequence, or wherein
   the base of the nucleotide at the 3' end of the first sequence is covalently bonded to the base of the nucleotide at the 3' end of the second sequence.

4. The oligonucleotide of claim 1 wherein
   the base of the nucleotide at the 5' end of the first sequence is covalently bonded to the 5' position of the nucleotide at the 5' end of the second sequence, or wherein
   the 5' position of the nucleotide at the 5' end of the first sequence is covalently bonded to the base of the nucleotide at the 5' end of the second sequence, or wherein
   the base of the nucleotide at the 3' end of the first sequence is covalently bonded to the 3' position of the nucleotide at the 3' end of the second sequence, or wherein
   the 3' position of the nucleotide at the 3' end of the first sequence is covalently bonded to the base of the nucleotide at the 3' end of the second sequence.

5. The oligonucleotide of claim 1 wherein said first and second sequences are covalently bonded through a linkage comprising a linker residue wherein said linker residue is of a molecule comprising two functional groups involved in the linkage, each said functional group selected from the group consisting of an amine, a sulfhydryl, and a hydroxyl.

6. The oligonucleotide of claim 5 wherein said linker residue is a residue of a diol or diamine.

7. The oligonucleotide of claim 6 wherein said diol or diamine is of the formula:
   $HZ(CH_2)_{n1}ZH$,
   wherein each Z is independently O or NH, and
   wherein n1 is an integer of 1–15 and one or more of said CH$_2$ groups may be replaced by O, S, or NH, provided said replacement is not adjacent to a heteroatom.

8. The oligonucleotide of claim 7 wherein the diol or diamine is of the formula
   $HZ(CH_2CH_2O)_{n2}H$,
   wherein Z is O or NH and
   wherein n2 is an integer of 1–5.

9. The oligonucleotide of claim 6 wherein said diol or diamine is of the formula
   $HZCH_2(CX_2CX_2)_{n3}CH_2ZH$,
   wherein each Z is independently O or NH, and
   wherein n3 is an integer of 1–7 and each pair of X or adjacent C independently are H or together are a π bond.

10. The diol or diamine of claim 6 wherein said diol or diamine is of the formula
    $HZCH_2(CX_2CX_2)_{n4}CH_2(CX_2CX_2)_{n5}CH_2ZH$,
    wherein each Z is independently O or NH, and
    wherein n4 and n5 are integers of 0–7 and wherein the sum of n4 and n5 is not greater than 7 and wherein each pair of X or adjacent C independently are H or together are a π bond.

11. The oligonucleotide of claim 6 wherein said diol or diamine contains a ring system.

12. The oligonucleotide of claim 11 wherein said ring system is nonaromatic.

13. The oligonucleotide of claim 12 wherein said nonaromatic ring is piperidine, piperazine, furan, tetrahydrofuran, cyclohexene, cyclopentene, cyclopentane or cyclohexane.

14. The oligonucleotide of claim 13 wherein the diol is selected from the group consisting of cis- or trans-3-4-dihydroxyfuran, cis- or trans-2-hydroxymethyl-3-hydroxyfuran, and cis- or trans-2-hydroxymethyl-4-hydroxyfuran, said furan either further unsubstituted, or further substituted with one or two noninterfering alkyl(1–4C) substituents.

15. The oligonucleotide of claim 11 wherein said ring system is aromatic.

16. The oligonucleotide of claim 15 wherein said aromatic ring is benzene or naphthalene.

17. The oligonucleotide of claim 16 wherein said diol is selected from the group consisting of 1,2-dihydroxymethylbenzene; 1,4-dihydroxymethylbenzene; 1,3-dihydroxymethylbenzene; 2,6-dihydroxymethylnaphthalene; 1,5-dihydroxymethylnaphthalene; 1,4-bis(3-hydroxypropenyl)benzene; 1,3-bis(3-hydroxypropenyl)benzene; 1,2-bis(3-hydroxypropenyl)benzene; 2,6-bis(3-hydroxypropenyl)naphthalene; 1,5-bis(3-hydroxypropynyl)naphthalene, 1,4-bis(3-hydroxypropynyl)benzene; 1,3-bis(3-hydroxypropynyl)benzene; 1,2-bis(3-hydroxypropynyl)benzene; 2,6-bis(3-hydroxypropynyl) naphthalene; and 1,5-bis(3-hydroxypropynyl)naphthalene.

18. The oligonucleotide of claim 1 wherein said first and second sequence are covalently bonded through a linkage of the formula:

$$X-\underset{Y}{\overset{\overset{X}{\|}}{P}}{\left[-X-A-X-\underset{Y}{\overset{\overset{X}{\|}}{P}}-\right]}_n X-$$

wherein:
Y is H, —OR, —SR, —NR$_2$, O$^{31}$, or S—;
X is O, S, or NR;
wherein each R is independently H, alkyl (1–12C), aryl (6–12C), aralkyl (7–20C) or alkaryl (7–20C);
n is 0 or 1; and
A is the residue of a linker group wherein said residue of a linker group is of a molecule comprising two functional groups involved in the linkage, each said functional group selected from the group consisting of an amine, a sulfhydryl, and a hydroxyl.

19. The oligonucleotide of claim 18 wherein all X are O.

20. The oligonucleotide of claim 19 wherein all Y are O.

21. The oligonucleotide of claim 18 wherein said linker residue, A, is a residue of a diol or diamine.

22. The oligonucleotide of claim 21 wherein said linker residue comprises a ring system.

23. The oligonucleotide of claim 22 wherein said ring is aromatic.

24. The oligonucleotide of claim 23 wherein said aromatic ring is benzene or naphthalene.

25. The oligonucleotide of claim 24 wherein said diol is selected from the group consisting of 1,2-dihydroxymethylbenzene; 1,4-dihydroxymethylbenzene; 1,3-dihydroxymethylbenzene; 2,6-dihydroxymethylnaphthalene; 1,5-dihydroxymethylnaphthalene; 1,4-bis(3-hydroxy propenyl)benzene; 1,3-bis(3-hydroxypropenyl)benzene; 1,2-bis(3-hydroxypropenyl)benzene; 2,6-bis(3-hydroxypropenyl)naphthalene; 1,5-bis(3-hydroxypropenyl) naphthalene; 1,4-bis(3-hydroxypropynyl)benzene; 1,3-bis(3-hydroxypropynyl)benzene; 1,2-bis(3-hydroxypropynyl)benzene; 2,6-bis(3-hydroxypropynyl) naphthalene; and 1,5-bis(3-hydroxypropynyl)naphthalene.

26. The oligonucleotide of claim 22 wherein said ring is nonaromatic.

27. The oligonucleotide of claim 26 wherein said nonaromatic ring is piperidine, piperazine, furan, tetrahydrofuran, cyclohexene, cyclopentene, cyclopentane or cyclohexane.

28. The oligonucleotide of claim 27 wherein the diol is selected from the group consisting of cis- or trans-3-4-dihydroxyfuran, cis- or trans-2-hydroxymethyl-3-hydroxyfuran and cis- or trans-2-hydroxymethyl-4-hydroxyfuran, said furan either further unsubstituted, or further substituted with one or two noninterfering alkyl (1-4C) substituents.

29. The oligonucleotide of claim 21 wherein said diol or diamine is of the formula:

$HZ(CH_2)_{n1}ZH$, wherein each Z is independently O or NH, and wherein n1 is an integer of 1–10 and one or more of said $CH_2$ groups may be replaced by O, S, or NH, provided said replacement is not adjacent to a heteroatom.

30. The oligonucleotide of claim 29 wherein the diol or diamine is of the formula $HZ(CH_2CH_2O)_{n2}H$, wherein Z is O or NH and wherein n2 is an integer of 1–5.

31. The oligonucleotide of claim 22 wherein said diol or diamine is of the formula $HZCH_2(CX_2CX_2)_{n3}CH_2ZH$, wherein each Z is independently O or NH, and wherein n3 is an integer of 1–7 and each pair of X is an adjacent C independently H or a $\pi$ bond.

32. The oligonucleotide of claim 21 wherein said diol or diamine is of the formula $HZCH_2(CX_2CX_2)_{n4}CH_2(CX_2CX_2)_{n5}CH_2ZH$, wherein each Z is independently O or NH, and wherein n4 and n5 are integers of 0–7 and wherein the sum of n4 and n5 is not greater than 7 and wherein each pair of X is an adjacent C independently H or a participant in a $\pi$ bond.

* * * * *